US012722284B2

(12) United States Patent
Seo et al.

(10) Patent No.: US 12,722,284 B2
(45) Date of Patent: Sep. 1, 2026

(54) MULTIPLE HELIX FLEXIBLE MECHANISM

(71) Applicant: PERAZAH INC., Ansan-si (KR)

(72) Inventors: Jong Tae Seo, Gwangju-si (KR); Hwan Taek Ryu, Ansan-si (KR)

(73) Assignee: PERAZAH INC., Ansan-si (KR)

( * ) Notice: Subject to any disclaimer, the term of this patent is extended or adjusted under 35 U.S.C. 154(b) by 0 days.

(21) Appl. No.: 18/272,801

(22) PCT Filed: Jan. 19, 2022

(86) PCT No.: PCT/KR2022/000963
§ 371 (c)(1),
(2) Date: Jul. 18, 2023

(87) PCT Pub. No.: WO2022/158841
PCT Pub. Date: Jul. 28, 2022

(65) Prior Publication Data

US 2024/0300089 A1 Sep. 12, 2024

(30) Foreign Application Priority Data

Jan. 19, 2021 (KR) ........................ 10-2021-0007614

(51) Int. Cl.
*B25J 9/10* (2006.01)
*A61B 1/005* (2006.01)

(52) U.S. Cl.
CPC ............. *B25J 9/104* (2013.01); *A61B 1/0057* (2013.01)

(58) Field of Classification Search
CPC ...... A61B 1/0011; A61B 1/0057; B25J 9/104; B25J 9/0006; B25J 15/0009; B25J 17/0258
See application file for complete search history.

(56) References Cited

U.S. PATENT DOCUMENTS 5,531,664 A * 7/1996 Adachi ................ A61B 1/0052 600/152
10,463,848 B2 11/2019 Régnier et al.
2014/0107455 A1 4/2014 Régnier et al.
(Continued)

FOREIGN PATENT DOCUMENTS

EP 3305163 A1 4/2018
JP 5875043 B2 3/2016
(Continued)

OTHER PUBLICATIONS

International search report of PCT/KR2022/000963, Apr. 22, 2022, English translation.

(Continued)

*Primary Examiner* — Joseph Brown
(74) *Attorney, Agent, or Firm* — STIP Law Group, LLC

(57) ABSTRACT

The present invention comprises a plurality of flexible tubes, wherein each of the plurality of flexible tubes includes at least two steering wires linearly arranged therein in the longitudinal direction thereof so as to transfer an operating force applied to one longitudinal end thereof to an end effector connected to the other longitudinal end thereof, and the number of the provided flexible tubes is at least two, and the at least two flexible tubes may be twisted in a spiral shape along the longitudinal direction thereof to form a flexible tube group.

10 Claims, 14 Drawing Sheets
(3 of 14 Drawing Sheet(s) Filed in Color)

(56) References Cited

U.S. PATENT DOCUMENTS

2017/0332882 A1* 11/2017 Yamamoto ........... A61B 1/0016
2019/0387959 A1* 12/2019 Yi ........................ A61B 1/0057
2020/0383740 A1 12/2020 Hyodo et al.

FOREIGN PATENT DOCUMENTS

| | | | |
|---|---|---|---|
| KR | 20050025681 | A | 3/2005 |
| KR | 200444288 | Y1 | 4/2009 |
| KR | 20120112273 | A | 10/2012 |
| KR | 20130075932 | A | 7/2013 |
| KR | 20200026132 | A | 3/2020 |
| WO | WO2015093602 | A1 | 6/2015 |
| WO | WO2017175373 | A1 | 10/2017 |
| WO | WO2020046035 | A1 | 3/2020 |

OTHER PUBLICATIONS

The extended European search report of EP 22 74 2817, Nov. 28, 2024.

* cited by examiner

[FIG. 1]
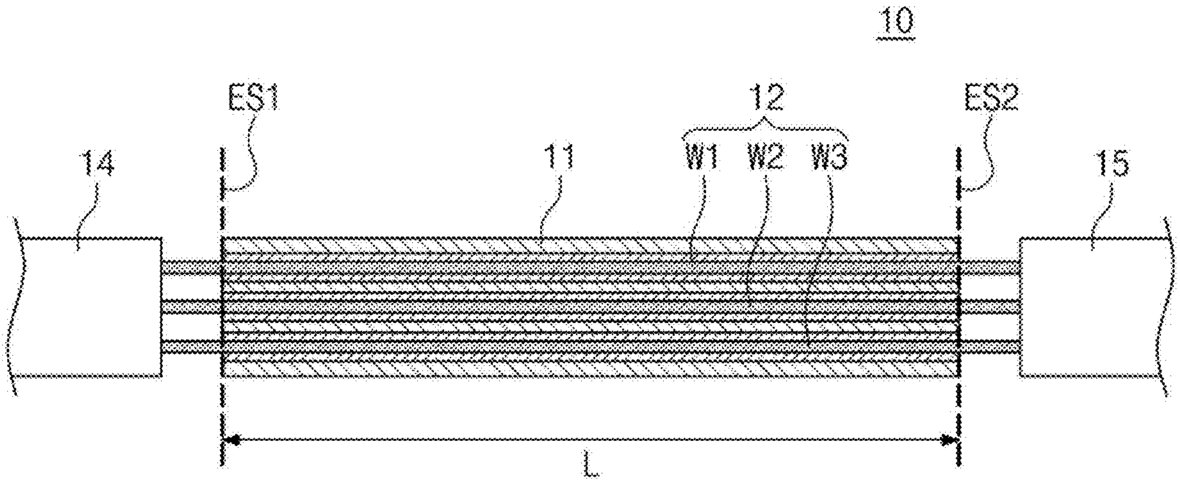
-- Prior Art --

[FIG. 2]
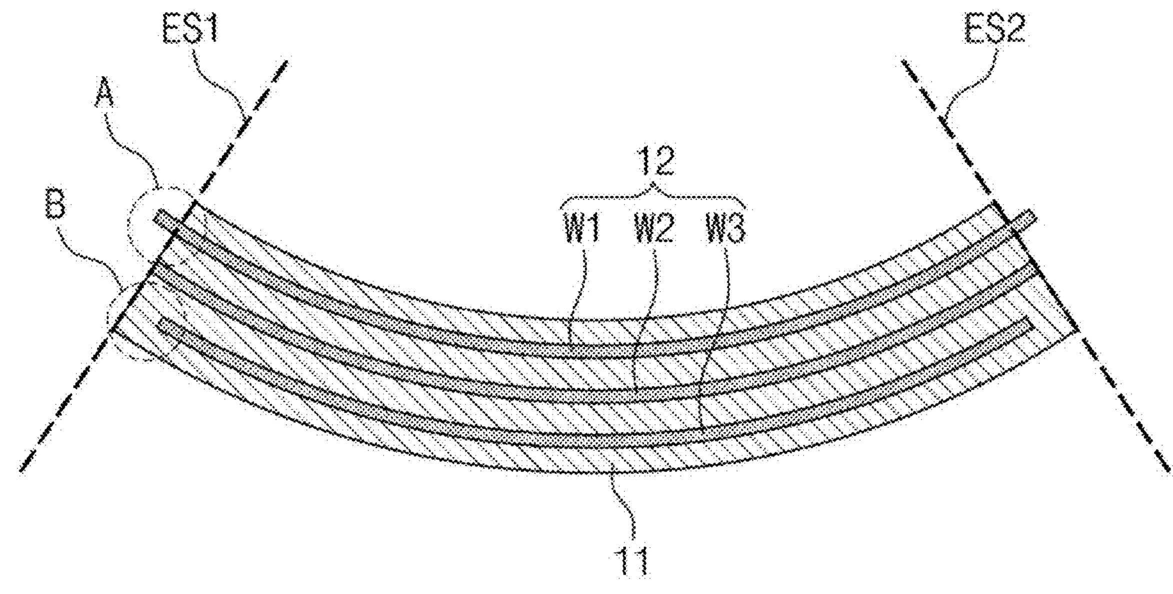
-- Prior Art --

[FIG. 3]
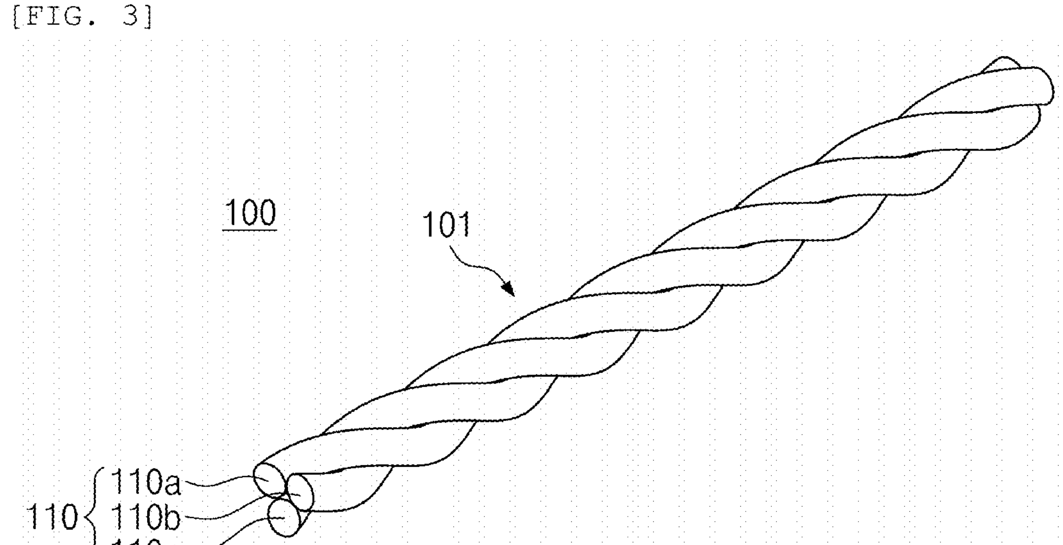

[FIG. 4]
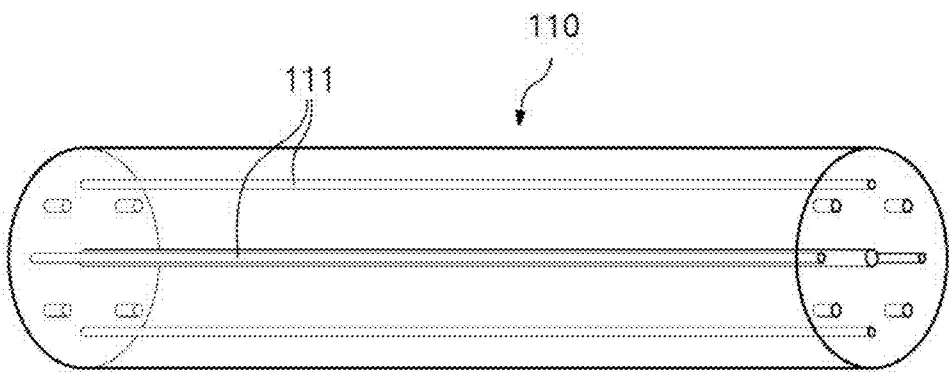

[FIG. 5]
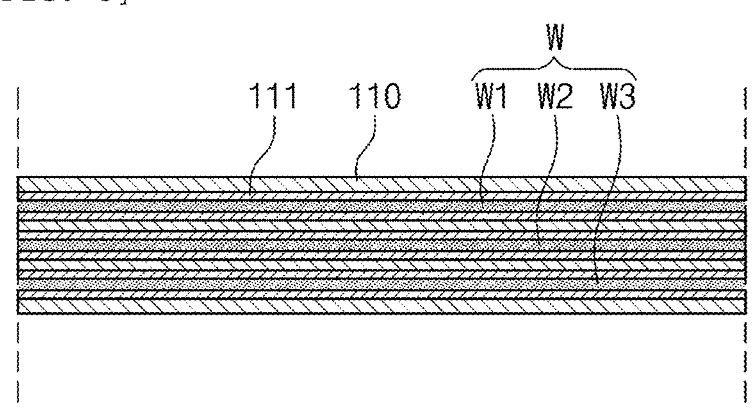

[FIG. 6]
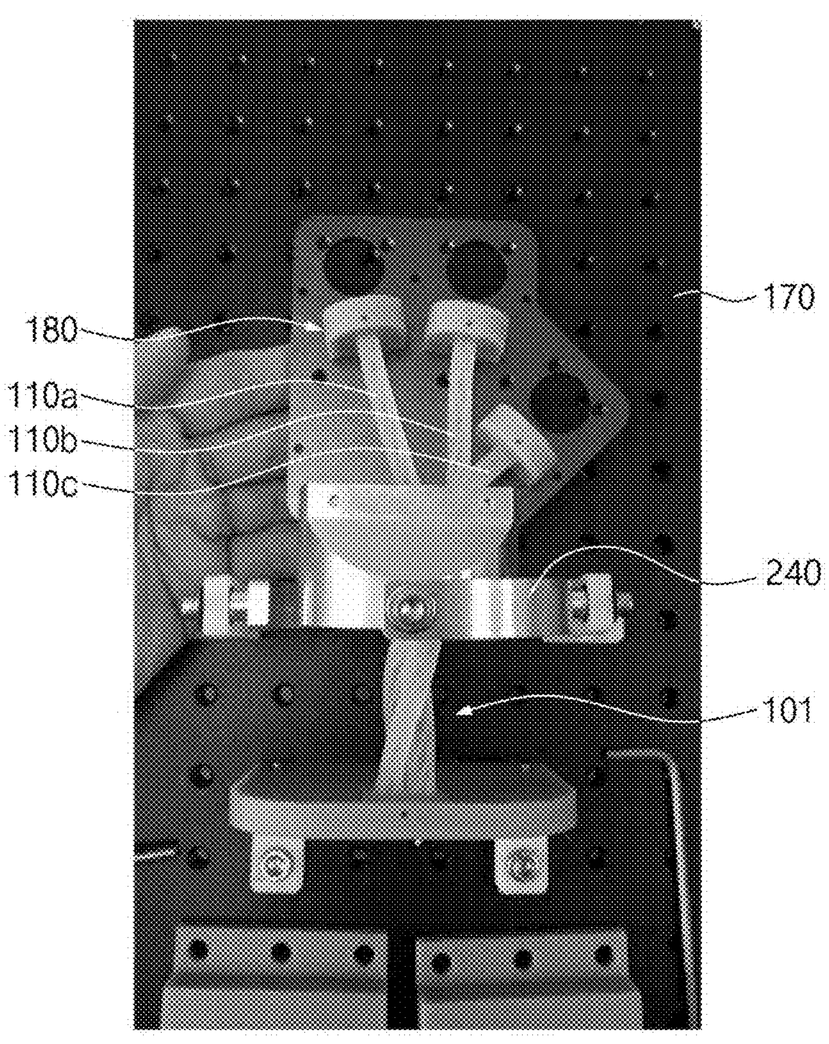

[FIG. 7]
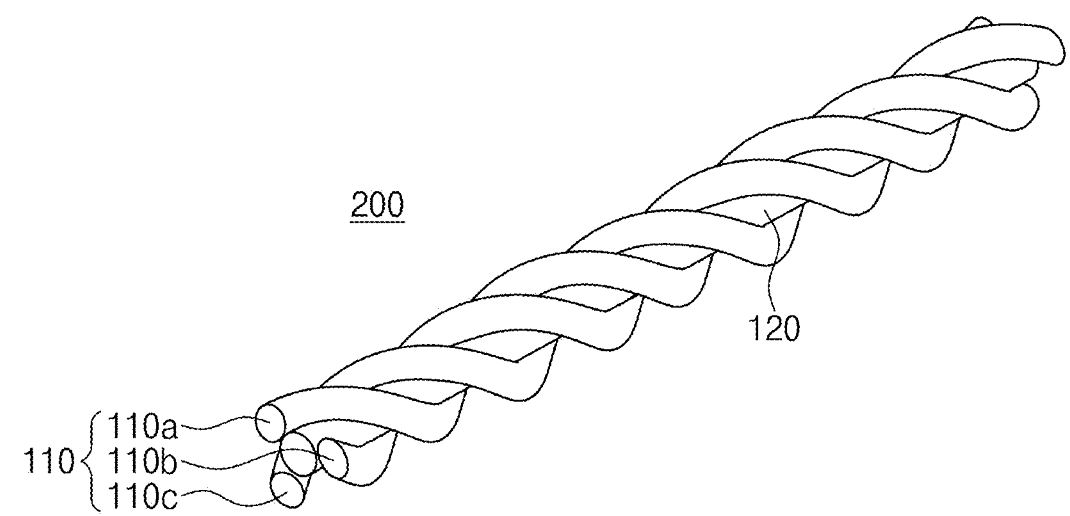

[FIG. 9]
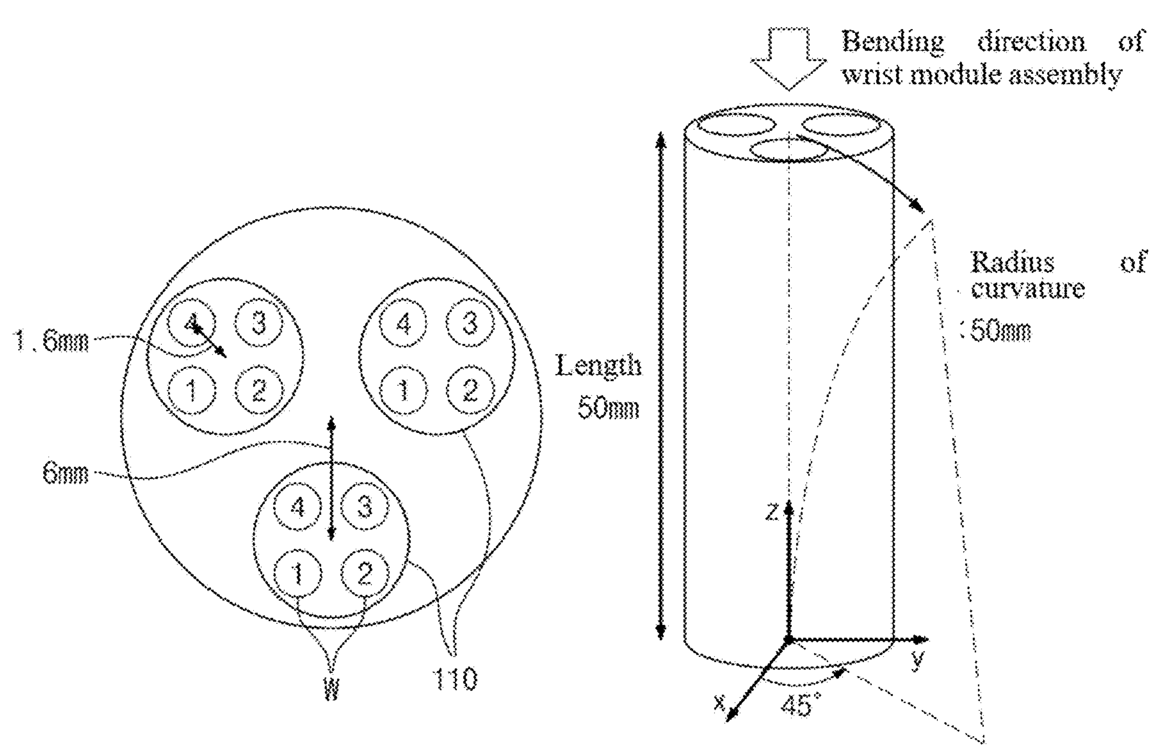

[FIG. 10]
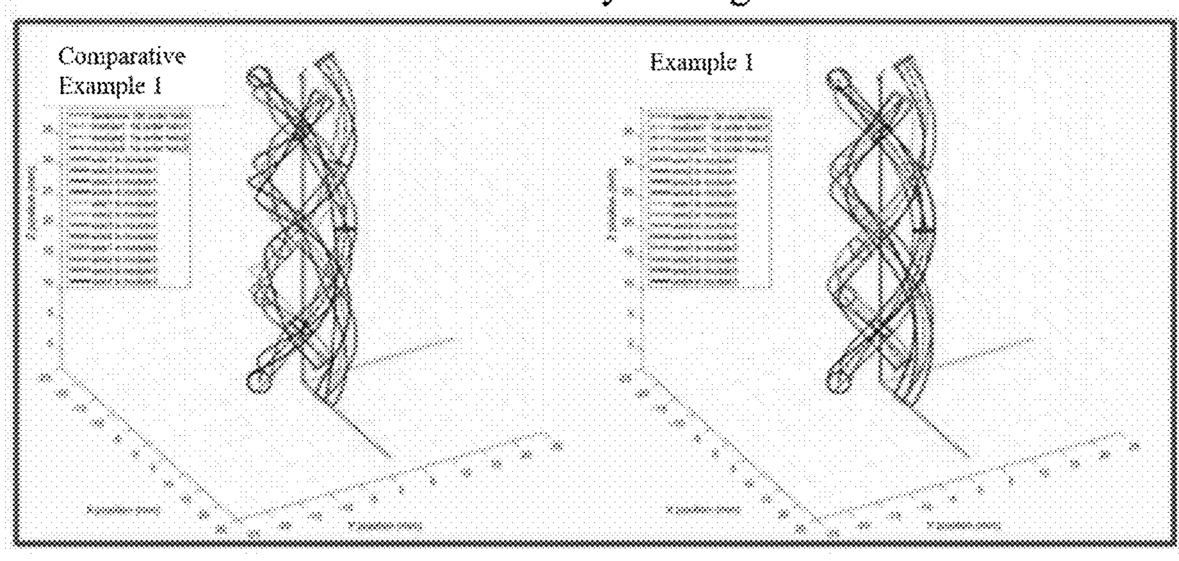

[FIG. 11]
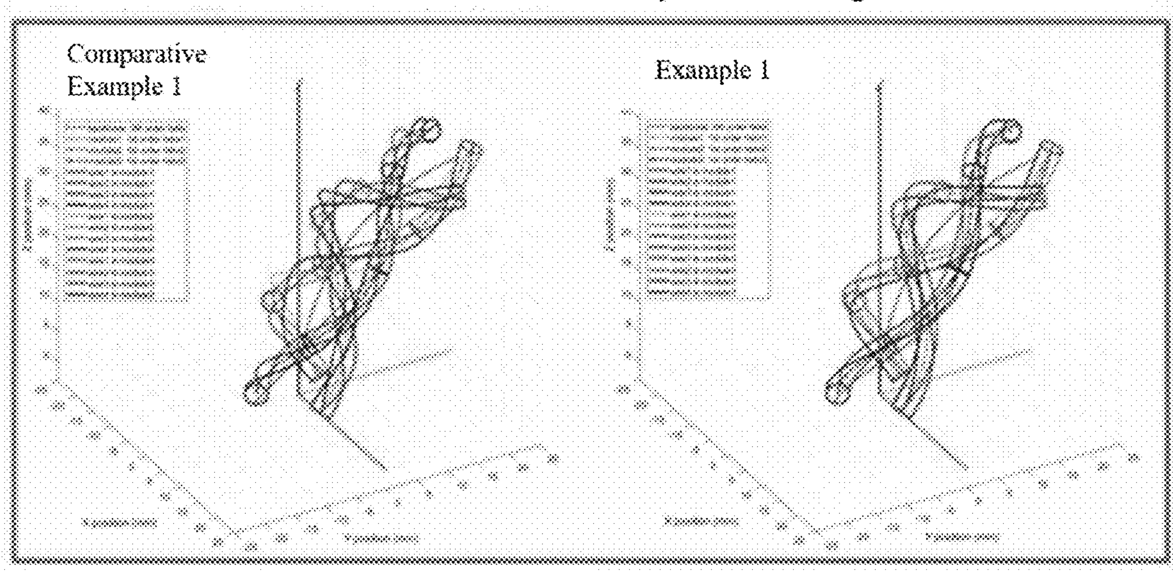

[FIG. 12]
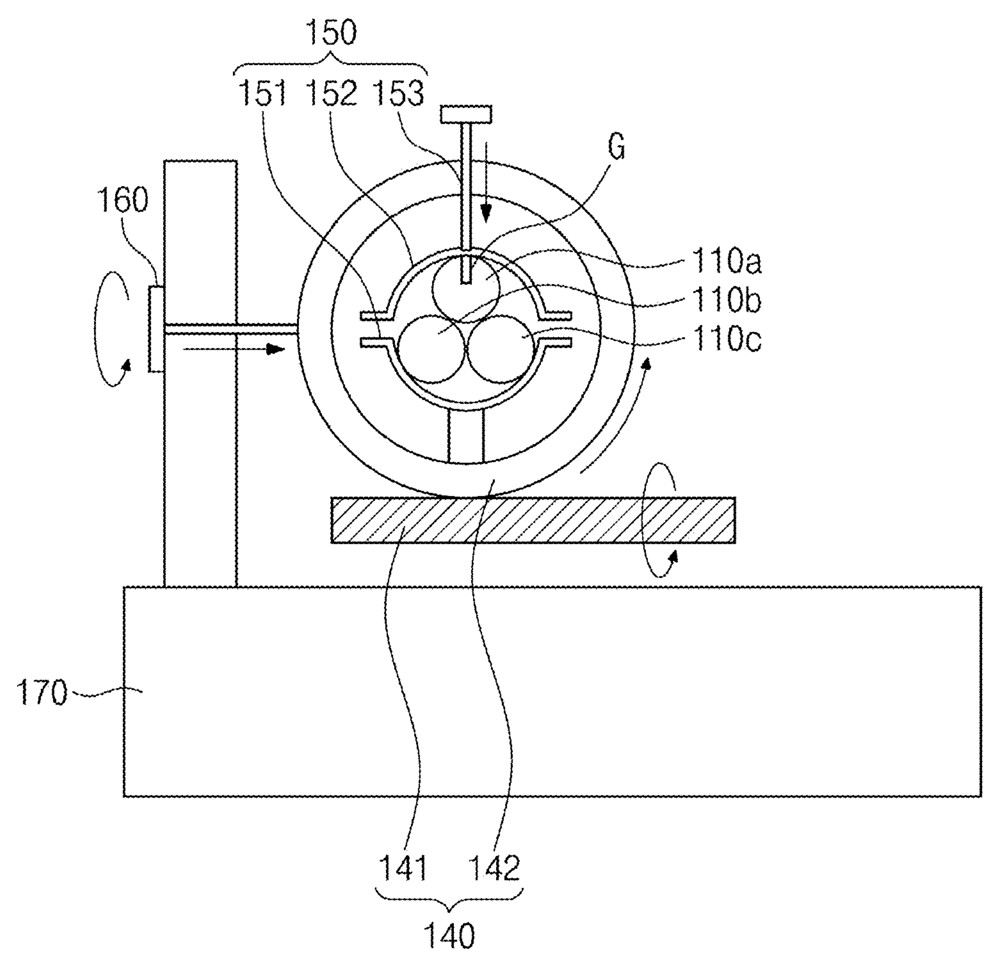

[FIG. 13]
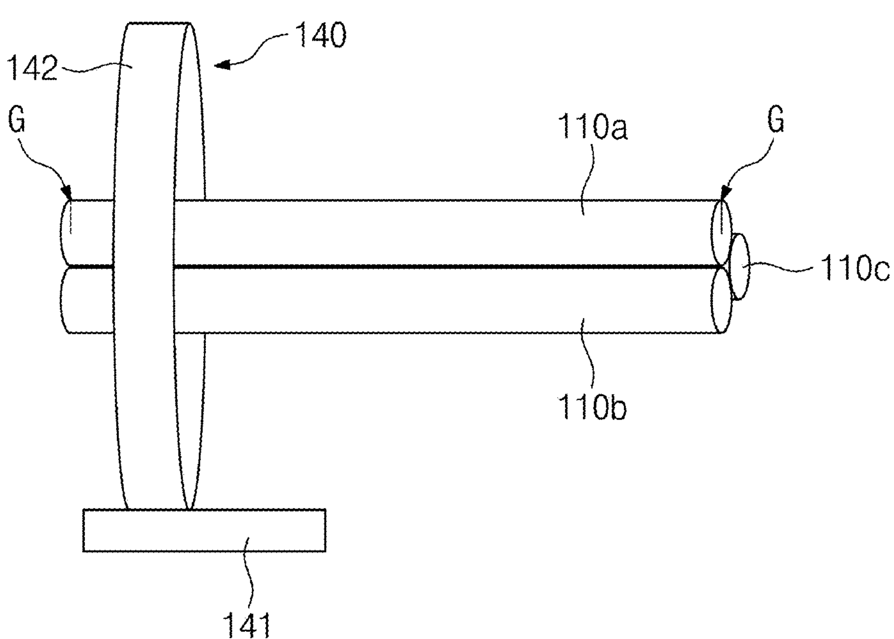

[FIG. 14]

MULTIPLE HELIX FLEXIBLE MECHANISM

CROSS-REFERENCE TO RELATED APPLICATIONS

This application is the U.S. National Phase under 35 U.S.C. § 371 of International Application No. PCT/KR2022/000963, filed on Jan. 19, 2022, which in turn claims the benefit of Korean Application No. 10-2021-0007614, filed on Jan. 19, 2021, the disclosures of which are incorporated by reference into the present application.

TECHNICAL FIELD

The present invention relates to a multiple helix flexible mechanism, and more specifically, to a multiple helix flexible mechanism, which may prevent a wire from getting slack to smoothly control an operation of an end effector mounted on an end of the multiple helix flexible mechanism, in which at least two flexible tubes are twisted in a spiral shape along a longitudinal direction, and a steering wire is linearly arranged inside each of the flexible tubes in a longitudinal direction.

BACKGROUND ART

A flexible mechanism may be used for medical purposes for observing or treating a narrow space with a bend or for a robot for controlling an end effector of the robot.

In order to describe the conventional flexible mechanism in more detail, reference will be made to FIGS. 1 and 2.

Referring to FIG. 1, the conventional flexible mechanism 10 may include a backbone 11, a plurality of steering wires W1, W2 and W3; 12, a handler 14 serving as a steering operation device, and an end effector 15. The backbone 11 is drawn into a predetermined path and is bent along the path. The steering wire 12 is arranged along the longitudinal direction of the backbone 11 and transfers the operation force provided from the handler 14 to the end effector 15.

As such, when the operating force is transferred from the handler 14 to the end effector 15 through the steering wire 12, an unintended operating force may be generated according to the posture of the backbone, that is, the bending of the path through which the backbone passes.

For a more detailed description, referring to FIG. 1, when the backbone 11 has a linear shape, a distance between a first end surface ES1 and a second end surface ES2 of the backbone 11 may be L. In this case, a distance between the first end surface ES1 and the second end surface ES2 of the steering wires W1, W2 and W3 provided inside the backbone 11 may also be the same as L. At that time, the length of the backbone 11 and the lengths of the steering wires W1, W2 and W3 are the same as each other, and thus it may be understood that a relative displacement is 0.

In this case, as shown in FIG. 2, when bending occurs to the flexible mechanism 10, a relative displacement may occur between the backbone 11 and the steering wire 12. For example, referring to region A shown in FIG. 2, the first steering wire W1 protrudes past the first end surface ES1 and the second end surface ES2. As another example, referring to region B shown in FIG. 2, the third steering wire W3 does not reach between the first end surface ES1 and the second end surface ES2.

In this case, an unintended change occurs in the tension applied by the steering wires 12 to the end effector 15, and thus may cause a problem in which unintended manipulation occurs. Accordingly, there has been a problem in that the operation of the end effector 5 is not easily controlled and the steering wire 12 is frequently broken.

Meanwhile, when the diameter of the flexible mechanism needs to be small due to the characteristics of the field to which the flexible mechanism is applied, it is difficult to insert a large number of steering wires into one flexible mechanism. In this case, a structure in which a plurality of flexible mechanisms are spirally wound may be used.

At this time, in the related art, the steering wires inserted into each flexible structure are also inserted through a spiral path to form a spirally wound structure.

Even in this case, however, when bending occurs to the flexible mechanism, there is a limit in solving a problem in which unintended manipulation occurs due to the pulling or loosening of the steering wires.

DISCLOSURE

Technical Problem

One technical object of the present invention is to provide a multiple helix flexible mechanism, which may prevent a wire from getting slack to smoothly control an operation of an end effector mounted on an end of the multiple helix flexible mechanism.

The technical objects of the present invention are not limited to the above.

Technical Solution

To solve the above technical objects, the present invention may provide a multiple helix flexible mechanism.

According to one embodiment, the multiple helix flexible mechanism may include a plurality of flexible tubes extending in a longitudinal direction, in which each of the plurality of flexible tubes may have at least two steering wires linearly arranged in the flexible tubes in a longitudinal direction so as to transfer an operating force applied to one longitudinal end of the flexible tube to an end effector connected to an opposite longitudinal end of the flexible tube, at least two flexible tubes may be provided, and the at least two flexible tubes may be twisted in a spiral shape along the longitudinal direction thereof to form a flexible tube group.

According to one embodiment, the multiple helix flexible mechanism may further include a flexible shaft extending in a longitudinal direction of the flexible tube, in which the at least two flexible tubes may be twisted and wound in a spiral shape along a longitudinal direction of an outer circumferential surface of the flexible shaft.

According to one embodiment, the at least two flexible tubes may be alternately twisted and wound in the same cycle.

According to one embodiment, a cycle in which the at least two flexible tubes are twisted and wound may be a multiple of 360 degrees.

According to one embodiment, the flexible tube may include at least one linear tunnel which is provided at an inside of the flexible tube in a longitudinal direction, and any one of the steering wires may be inserted through any one of the linear tunnels.

According to one embodiment, the multiple helix flexible mechanism may further include a housing tube, in which the housing tube may extend in a longitudinal direction, and the flexible tube group may be arranged in a longitudinal direction inside the housing.

According to one embodiment, a spiral rail for providing a spiral path of the flexible tube group may be provided inside the housing tube.

According to one embodiment, the multiple helix flexible mechanism may include: a worm gear including a worm and a worm wheel rotating in engagement with the worm; a clamping member provided at an inner diameter side of the worm wheel and fastened to an outer circumferential surface at one longitudinal end side of the flexible tube group passing through the inner diameter side of the worm wheel; a worm wheel fixing pin configured to restrict rotation of the worm wheel by pressing one side of an outer diameter side of the worm wheel so that a twisted structure of the flexible tube group is maintained, when the flexible tube group is twisted and wound at a multiple of 360 degrees by rotation of the worm wheel; and a mount unit for supporting the worm wheel fixing pin.

According to one embodiment, the clamping member may include: a first clamp fixed to the inner diameter side of the worm wheel; a second clamp arranged to be symmetrical to the first clamp with the flexible tube group interposed therebetween; and a clamp pressing pin connected to the second clamp and configured to press the second clamp toward the first clamp side through a fastening force with respect to the worm wheel to fix the flexible tube group wrapped by the first clamp and the second clamp.

According to one embodiment, alignment notches may be collinearly marked on one longitudinal end and an opposite end of the flexible tube group, in order to determine whether or not the flexible tube group is twisted and wound at a multiple of 360 degrees.

Advantageous Effects

According to an embodiment of the present invention, the multiple helix flexible mechanism may include a plurality of flexible tubes extending in a longitudinal direction, in which each of the plurality of flexible tubes may have at least two steering wires linearly arranged in the flexible tubes in a longitudinal direction so as to transfer an operating force applied to one longitudinal end of the flexible tube to an end effector connected to an opposite longitudinal end of the flexible tube, at least two flexible tubes may be provided, and the at least two flexible tubes may be twisted in a spiral shape along the longitudinal direction thereof to form a flexible tube group.

Accordingly, there may be provided the multiple helix flexible mechanism capable of preventing a wire from getting slack, thereby smoothly controlling an operation of an end effector mounted on an end of the multiple helix flexible mechanism.

In other words, according to an embodiment of the present invention, there may be provided the multi-helix flexible mechanism capable of preventing or minimizing a problem in which an unintended manipulation for the end effector occurs due to an unintended change in tension applied to the end effector.

According to an embodiment of the present invention, there may be provided the multiple helix flexible mechanism capable of more smoothly performing a steering operation of the end effector connected to an end of an endoscope and also extending a lifespan, when applied to the endoscope.

In addition, according to an embodiment of the present invention, there may be provided the multiple helix flexible mechanism applicable to a manual tool used for single-channel laparoscopic surgery.

Furthermore, according to an embodiment of the present invention, there may be the multiple helix flexible mechanism which may be widely applied to various implantable diagnostic and treatment devices inserted into a curved human body.

Moreover, according to an embodiment of the present invention, there may be provided the multiple helix flexible mechanism which may be easily applied to an industrial endoscope for diagnosing the inside of a curved pipeline, an entertainment device in which a long curve occurs, a long curved device inserted for a rescue operation in a disaster phenomenon, and the like.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1 and 2 are views for explaining a conventional flexible mechanism.

FIG. 3 is a view for explaining a flexible tube group of a flexible mechanism according to one embodiment of the present invention.

FIG. 4 is a view for explaining a flexible tube of a flexible mechanism according to one embodiment of the present invention.

FIG. 5 is a sectional view showing a flexible mechanism according to one embodiment of the present invention.

FIG. 6 is a view showing a flexible mechanism according to one embodiment of the present invention, in which an end effector is connected to an end of the flexible mechanism.

FIG. 7 is a view for explaining a flexible mechanism according to another embodiment of the present invention.

FIG. 8 is a view for explaining a flexible mechanism according to still another embodiment of the present invention.

FIGS. 9 to 11 are views for explaining the results of an experiment on an embodiment and a comparative example of the present invention.

FIGS. 12 to 14 are views for explaining a flexible mechanism according to a modified embodiment of the present invention.

BEST MODE

Hereinafter, preferred embodiments of the present invention will be described in detail with reference to the accompanying drawings. However, the technical spirit of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, a shape and a size are exaggerated for efficient description of the technical contents.

In addition, in the various embodiments of the present specification, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. Each of the embodiments described and illustrated herein also include their complementary embodiments. Further, the term "and/or" in the present specification is used to include at least one of the elements enumerated in the specification.

In the specification, the terms of a singular form may include plural forms unless otherwise specified. Further, the terms "including" and "having" are used to designate that the features, the numbers, the steps, the elements, or combinations thereof described in the specification are present, and are not to be understood as excluding the possibility that one or more other features, numbers, steps, elements, or combinations thereof may be present or added. In addition, the term "connection" used herein may include the meaning of indirectly connecting a plurality of components, and directly connecting a plurality of components.

Further, in the following description of the present invention, a detailed description of known functions and configurations incorporated herein will be omitted when it may make the subject matter of the present invention unnecessarily unclear.

FIG. 3 is a view for explaining a flexible tube group of a flexible mechanism according to one embodiment of the present invention, FIG. 4 is a view for explaining a flexible tube of a flexible mechanism according to one embodiment of the present invention, FIG. 5 is a sectional view showing a flexible mechanism according to one embodiment of the present invention, and FIG. 6 is a view showing a flexible mechanism according to one embodiment of the present invention, in which an end effector is connected to an end of the flexible mechanism.

As shown in FIGS. 3 to 5, the multiple helix flexible mechanism 100 according to one embodiment of the present invention may include a flexible tube 110 and a wire W.

The flexible tube 110 may perform a function of providing a predetermined path. For example, when the multiple helix flexible mechanism 100 is used for a medical purpose, the flexible tube 110 may move in a human body, for example, along a large intestine, esophagus, or the like. In this case, the flexible tube 110 may be made of a flexible material which may be bent along curves in the human body.

The flexible tube 110 moves through an internal path of the human body, and thus may of course be made of a body-friendly material. As another example, the flexible tube 110 may be made of a flexible material, even when is used for the purpose of a robot.

The flexible tube 110 may be provided in a cylindrical shape extending in a longitudinal direction. A steering operation device connected to each of one longitudinal end and an opposite end of the flexible tube 110 as well as a steering wire W connecting an end effector (180 of FIG. 6) may be arranged in the flexible tube 110.

Referring to FIG. 4, for this purpose, the flexible tube 110 may include linear tunnels 111 corresponding to the number of steering wires W.

The linear tunnel 111 may be provided at an inside of the flexible tube 110 in a longitudinal direction. The linear tunnel 111 may be provided in a cylindrical shape, and both longitudinal ends may be open. Accordingly, any one steering wire W may be inserted through any one linear tunnel 111 provided at an inside of the flexible tube 110.

Meanwhile, according to one embodiment of the present invention, at least two flexible tubes 110 may be provided. For example, the flexible tube 110 may be provided in a number selected from two, three, four, . . . , n. In this case, it may be preferable that the flexible tubes 110 are provided up to a maximum of 12.

Accordingly, the flexible tube 110 according to one embodiment of the present invention may include a first flexible tube 110*a*, a second flexible tube 110*b*, and a third flexible tube 110*c*.

As such, in one embodiment of the present invention, for convenience of description, it is assumed that the flexible tube 110 includes the first flexible tube 110*a*, the second flexible tube 110*b*, and the third flexible tube 110*c*, but this is only one example, and the technical spirit of the present invention is not limited thereto.

According to one embodiment of the present invention, the first flexible tube 110*a*, the second flexible tube 110*b*, and the third flexible tube 110*c* may be spirally twisted along the longitudinal direction, that is, simulate a DNA structure to form one flexible tube group 101.

In this case, the first flexible tube 110*a*, the second flexible tube 110*b*, and the third flexible tube 110*c* may be alternately wound in the same cycle. At this time, a cycle in which the first flexible tube 110*a*, the second flexible tube 110*b*, and the third flexible tube 110*c* are twisted and wound may be a multiple of 360 degrees.

According to one embodiment, the first flexible tube 110*a* may be twisted in a spiral shape while rotating in a clockwise direction. In addition, the second flexible tube 110*b* may be spirally wound in the longitudinal direction on an outer circumferential surface of the first flexible tube 110*a* while rotating in the counterclockwise direction. Furthermore, the third flexible tube 110*c* may be spirally wound in the longitudinal direction on an outer circumferential surface of the first flexible tube 110*a* and the second flexible tube 110*b* while rotating in the counterclockwise direction.

In this case, the first flexible tube 110*a*, the second flexible tube 110*b*, and the third flexible tube 110*c* may have the same cycle and a phase within the cycle. In other words, the first flexible tube 110*a*, the second flexible tube 110*b*, and the third flexible tube 110*c* may have the same node and antinode.

Here, a DNA simulation shape of the flexible tube group 101 may be maintained by spirally twisting and winding the first flexible tube 110*a*, the second flexible tube 110*b*, and the third flexible tube 110*c* along the longitudinal direction, impregnating the same in an UV curable material, taking the same out, and irradiating the same with UV rays. However, this is only one example, and the technical idea of the present invention is not limited thereto.

Referring to FIG. 5, the steering wire W may be linearly arranged along the longitudinal direction of the flexible tube 110. Specifically, the steering wire W may be inserted through the linear tunnel 111 formed in the longitudinal direction of the flexible tube 110, and thus may be linearly arranged in the longitudinal direction of the flexible tube 110.

By adjusting the tension according to the operating force applied to the steering operation device connected to one longitudinal end, the steering wire W may transfer a driving force capable of controlling the end effector (180 in FIG. 6) connected to an opposite longitudinal end.

A plurality of the steering wires W may be provided. For example, when n steering wires W are provided, the n steering wires W may control n−1 degrees of freedom of the end effector (180 in FIG. 6). Here, above n may be a natural number.

According to one embodiment of the present invention, the steering wire W may include a first steering wire W1, a second steering wire W2, and a third steering wire W3. Accordingly, the steering wire W may control two degrees of freedom of the end effector (180 in FIG. 6).

As such, in one embodiment of the present invention, for convenience of description, it is assumed that the steering wire W includes the first steering wire W1, the second steering wire W2, and the third steering wire W3, but this is only one example, and the technical spirit of the present invention is not limited thereto.

The first steering wire W1, the second steering wire W2, and the third steering wire W3 may be arranged at an inside of the first flexible tube 110*a*, the second flexible tube 110*b*, and the third flexible tube 110*c*, respectively. In this case, the first steering wire W1, the second steering wire W2, and the third steering wire W3 may be linearly arranged at an inside of the first flexible tube 110*a*, the second flexible tube 110*b*, and the third flexible tube 110*c*, respectively.

In other words, the first steering wire W1, the second steering wire W2, and the third steering wire W3 may be arranged in parallel with each other in the longitudinal direction at an inside of the first flexible tube 110*a*, the second flexible tube 110*b*, and the third flexible tube 110*c*, respectively.

In one embodiment of the present invention, the first flexible tube 110*a*, the second flexible tube 110*b*, and the third flexible tube 110*c* may have a shape which simulates a DNA structure, and may be arranged in a form of being spirally twisted and wound along the longitudinal direction. Accordingly, the first steering wire W1, the second steering wire W2, and the third steering wire W3 may be twisted in a spiral shape while keeping in parallel with each other.

The multiple helix flexible mechanism 100 according to one embodiment of the present invention may have at least two flexible tubes 110 spirally twisted and wound along the longitudinal direction as well as the steering wire W arranged in the linear direction in each of the flexible tubes 110. Thus, even when bending occurs to the flexible tube 110, it may be possible to minimize a phenomenon in which the steering wire described with reference to FIG. 2 unintentionally protrudes from or is inserted into one end of the backbone (flexible tube) so as to unintentionally control the end effector.

More specifically, the multiple helix flexible mechanism may have a structure in which at least two flexible tubes 110 having the steering wire W arranged in a linear direction at an inside of the flexible tube are spirally twisted and wound along the longitudinal direction, that is, a simulation structure which is the same or similar to a DNA structure. Thus, even when bending occurs to the flexible mechanism 100, a path of the steering wires W1, W2, and W3 may be constantly maintained.

When the flexible tube 110 is bent, an inner region of the flexible tube 110 may have a length shorter than that of an initial state, and an outer region thereof may have a length longer than that of the initial state. In this case, the steering wires W1, W2 and W3 may be linearly arranged at an inside of the flexible tubes 110, respectively, and thus may be affected by a change in the length generated both in the inner region and the outer region of the flexible tube 110.

At this time, the at least two flexible tubes 110 have a structure of being spirally twisted along the longitudinal direction, and thus a loosened region and a tight region of the steering wire W may be offset by each other. Accordingly, even when bending occurs to the flexible mechanism 100, the steering wires W1, W2 and W3 may maintain the same length between one longitudinal end and an opposite end of the flexible tube 110.

In order to obtain the effect as above, a cycle in which at least two flexible tubes 110 are wound may be a multiple of 360 degrees, and the steering wire W arranged at an inside of each flexible tube 110 may form a linear shape along the longitudinal direction of the flexible tube 110.

In this case, each of the flexible tubes 110 may be arranged to be opposite to each other in a spiral direction. On contrary, when respective flexible tubes 110 are arranged in the same spiral direction, there is no problem in an initial state in which the flexible tubes 110 are in a straight state, but when tension is applied to the steering wire W, the shape of the flexible tube 110 may not maintain a straight line and may be twisted.

It is understood that this causes deformation of the shape of the flexible tube 110 due to the force in which the steering wire W spirally arranged by the flexible tube 110 tends to be straightened when the steering wire W is pulled.

As such, according to one embodiment of the present invention, since respective flexible tubes 110 are spirally arranged in opposite directions to each other and the steering wire W is linearly arranged at an inside of the respective flexible tubes 110, even if the tension of the steering wire W increases, the deformation of the shape of the flexible tube 110 may be minimized.

Accordingly, according to one embodiment of the present invention, the steering wire W may be prevented from getting slack, and as a result, the operation of the end effector (180 of FIG. 6) connected to an end may be smoothly controlled.

In other words, according to one embodiment of the present invention, an unintended change may occur to the tension applied to the end effector (180 in FIG. 6), thereby preventing or minimizing a problem in which unintended operation of the end effector (180 in FIG. 6) occurs.

Accordingly, for example, when the multiple helix flexible mechanism 100 according to one embodiment of the present invention is applied to an endoscope, a steering operation of the end effector connected to an end of the multi-helix flexible mechanism 100 may be smoothly performed, a life span may be extended, and the multiple helix flexible mechanism may be applied to a manual tool used in single-channel laparoscopic surgery.

In other words, the multiple helix flexible mechanism 100 according to one embodiment of the present invention may have the effect as described above, and thus may be widely applied to various implantable diagnosis and treatment devices inserted into a curved human body.

In addition, the multiple helix flexible mechanism 100 according to one embodiment of the present invention may be easily applied to an industrial endoscope for diagnosing the inside of a curved pipeline, an entertainment device in which a long curve occurs, a long curved device inserted for a rescue operation in a disaster phenomenon, and the like.

FIG. 6 shows a state in which the multiple helix flexible mechanism 100 according to one embodiment of the present invention is applied to a hand for a robot.

Referring to FIG. 6, the flexible tube 110 may include a first flexible tube 110*a*, a second flexible tube 110*b*, and a third flexible tube 110*c*.

The first flexible tube 110*a*, the second flexible tube 110*b*, and the third flexible tube 110*c* may be spirally twisted along a longitudinal direction to form a flexible tube group 101.

In this case, the flexible tube group 101 may be connected to the end effector 180 through the gimbal 140 which provides a degree of freedom of rotation. The gimbal 140 may provide the end effector 180 with two degrees of freedom of rotation in horizontal and vertical axis directions based on the drawing.

According to one embodiment of the present invention, as the first flexible tube 110*a*, the second flexible tube 110*b*, and the third flexible tube 110*c*, having the steering wires linearly arranged at an inside, pass through the gimbal 140 while being wound in a spiral shape with each other, even if the gimbal 140 rotates, the tension state of the steering wires arranged at an inside of the first flexible tube 110*a*, the second flexible tube 110*b*, and the third flexible tube 110*c*, respectively, may be maintained without change.

Hereinafter, a multiple helix flexible mechanism according to another embodiment of the present invention will be described with reference to FIG. 7.

FIG. 7 is a view for explaining a flexible mechanism according to another embodiment of the present invention.

Referring to FIG. 7, a flexible mechanism 200 according to another embodiment of the present invention may include a flexible tube 110, a flexible shaft 120, and a steering wire W (see FIG. 5).

Since another embodiment of the present invention is different from one embodiment of the present invention only in that a flexible shaft is further provided, the same reference numerals may be assigned to the rest of the same components, and a detailed description thereof will be omitted.

According to another embodiment of the present invention, the flexible shaft 120 may extend in the longitudinal direction of the flexible tube 110.

The flexible shaft 120 may be provided in a cylindrical shape. The flexible shaft 120 may be made of a flexible material. The flexible shaft 120 may provide a winding path of the first flexible tube 110*a*, the second flexible tube 110*b*, and the third flexible tube 110*b*.

In other words, the first flexible tube 110*a*, the second flexible tube 110*b*, and the third flexible tube 110*b* may be spirally twisted and wound along the longitudinal direction of the outer circumferential surface of the flexible shaft 120.

As such, when the first flexible tube 110*a*, the second flexible tube 110*b*, and the third flexible tube 110*b* are spirally twisted and wound around the flexible shaft 120, the spirally twisted and wound shape may be supported by the flexible shaft 120, and thus the shape thereof may be more stably maintained.

Figure 8:
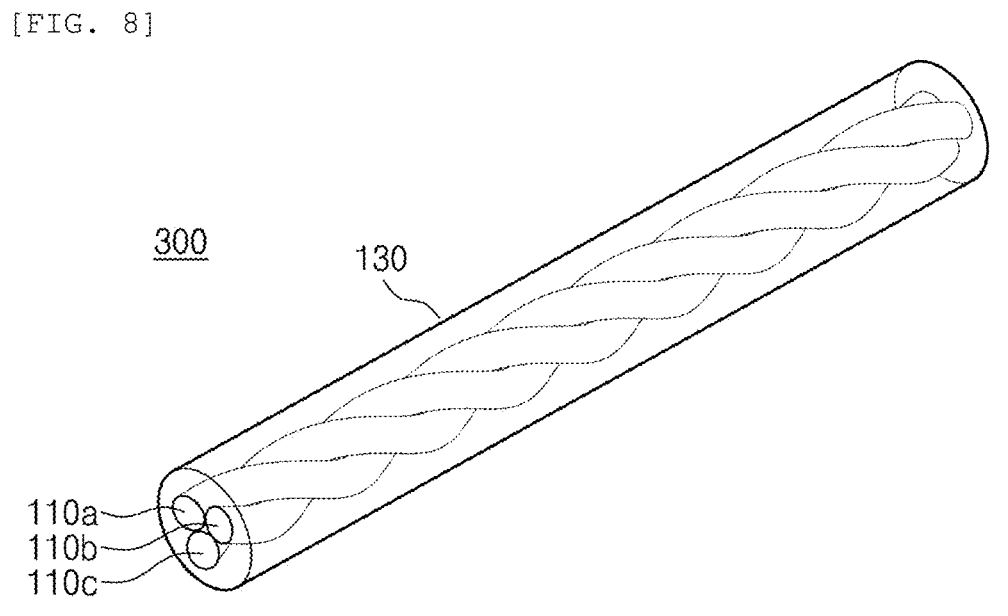

Hereinafter, a multiple helix flexible mechanism according to still another embodiment of the present invention will be described with reference to FIG. 8.

FIG. 8 is a view for explaining a flexible mechanism according to still another embodiment of the present invention.

Referring to FIG. 8, a flexible mechanism 300 according to still another embodiment of the present invention may include a flexible tube 110, a housing tube 130, and a steering wire W (see FIG. 5).

Since still another embodiment of the present invention is different from one embodiment of the present invention only in that a housing tube is further provided, the same reference numerals may be assigned to the rest of the same components, and a detailed description thereof will be omitted.

The housing tube 130 according to still another embodiment of the present invention may extend in the longitudinal direction of the flexible tube 110.

The housing tube 130 may be provided in a cylindrical shape. The housing tube 130 may be made of a flexible material. For example, the housing tube 130 may be made of the same material as that of the flexible tube 110.

The housing tube 130 may provide a space for mounting the flexible tube group 101 in which the flexible tube 110, more specifically, a plurality of flexible tubes 110*a*, 110*b*, and 110*c* are spirally twisted in the longitudinal direction.

For this purpose, a spiral rail for providing a spiral path of the flexible tube group 101 may be provided inside the housing tube 130.

As such, when the flexible tube group 101 having the first flexible tube 110*a*, the second flexible tube 110*b*, and the third flexible tube 110*b* spirally twisted is arranged inside the housing tube 130, the flexible tube group 101 may be supported by the housing tube 130, and thus the shape thereof may be more stably maintained.

Hereinafter, properties of a multiple helix flexible mechanism according to an embodiment of the present invention will be described with reference to FIGS. 9 to 11.

FIGS. 9 to 11 are views for explaining the results of an experiment on Example 1 of the present invention and Comparative Example 1.

Referring to FIG. 9, in Example 1, a wrist module was manufactured, in which three flexible tubes 110 (flexible tube 1, flexible tube 2, and flexible tube 3) were spirally twisted in a cycle of 360 degrees along the longitudinal direction, and four steering wires W, W1, W2, W3, and W4 were linearly arranged along the longitudinal direction of the flexible tube 110 at an inside of flexible tubes 110, respectively.

In Comparative Example 1, a wrist module was manufactured, in which three flexible tubes 110 (flexible tube 1, flexible tube 2, and flexible tube 3) were spirally twisted in a cycle of 360 degrees along the longitudinal direction, and four steering wires W, W1, W2, W3, and W4 were spirally twisted in a cycle of 360 degrees along the longitudinal direction of the flexible tube 110 at an inside of flexible tubes 110, respectively.

In this case, in order to calculate the length of the passage (lumen) (an inner tunnel of the flexible tube in which the steering wire is arranged), a discrete length integral method was used, and the simulation results thereof are shown in FIGS. 10 and 11, and Tables 1 to 6.

TABLE 1

| Comparative Example 1: Linear length (A) (mm) | W1 | W2 | W3 | W4 |
|---|---|---|---|---|
| Flexible tube 1 | 65.184 | 65.184 | 65.185 | 65.185 |
| Flexible tube 2 | 65.185 | 65.185 | 65.184 | 65.185 |
| Flexible tube 3 | 65.185 | 65.185 | 65.185 | 65.184 |

TABLE 2

| Comparative Example 1: Bending length (B) (mm) | W1 | W2 | W3 | W4 |
|---|---|---|---|---|
| Flexible tube 1 | 65.845 | 65.218 | 64.579 | 65.108 |
| Flexible tube 2 | 64.927 | 64.687 | 65.559 | 65.829 |
| Flexible tube 3 | 64.974 | 65.838 | 65.601 | 64.812 |

TABLE 3

| Comparative Example 1: Length change (A-B) (mm) | W1 | W2 | W3 | W4 |
|---|---|---|---|---|
| Flexible tube 1 | −0.660 | −0.033 | 0.606 | 0.077 |
| Flexible tube 2 | 0.258 | 0.497 | −0.374 | −0.644 |
| Flexible tube 3 | 0.211 | −0.653 | −0.415 | 0.372 |

TABLE 4

| Example 1: Linear length (C) (mm) | W1 | W2 | W3 | W4 |
|---|---|---|---|---|
| Flexible tube 1 | 67.375 | 67.375 | 58.887 | 58.215 |
| Flexible tube 2 | 57.335 | 64.682 | 68.931 | 62.606 |
| Flexible tube 3 | 64.683 | 57.335 | 61.575 | 68.572 |

TABLE 5

| Example 1: Bending length (D) (mm) | W1 | W2 | W3 | W4 |
|---|---|---|---|---|
| Flexible tube 1 | 67.449 | 67.450 | 58.902 | 58.231 |
| Flexible tube 2 | 57.354 | 64.724 | 69.028 | 62.631 |
| Flexible tube 3 | 64.724 | 57.354 | 61.594 | 68.663 |

TABLE 6

| Example 1: Length change (C-D) (mm) | W1 | W2 | W3 | W4 |
|---|---|---|---|---|
| Flexible tube 1 | −0.073 | −0.074 | −0.015 | −0.016 |
| Flexible tube 2 | −0.019 | −0.042 | −0.096 | −0.025 |
| Flexible tube 3 | −0.041 | −0.018 | −0.019 | −0.090 |

As shown in FIGS. 10 and 11 and above Tables 1 to 6, for each of the wrist modules of Example 1 and Comparative Example 1, changes in the lengths of the respective lumens were compared with each other when the wrist module is in an unfolded state and in a bent state. As a result, in the case of Example 1, it was measured that the changes in the lengths of the respective wires are −0.096 to −0.015 mm when the wrist module is straight and bent.

On contrary, in the case of Comparative Example 1, it was measured that the changes in the lengths of respective wires are −0.606 to 0.606 mm when the wrist module is straight and bent.

Accordingly, it was confirmed that in Example 1 in which the flexible tubes are spirally twisted along the longitudinal direction and the steering wires having a linear shape are arranged at an inside of respective flexible tubes, the tension applied by each of the steering wires to the end effector may be constantly maintained even when the wrist module is bent, as compared to Comparative Example 1 in which both the flexible tube and the steering wire are spirally twisted, and as a result, the steering wire may be prevented from getting slack.

As in Example 1, a structure in which a plurality of flexible tubes are spirally twisted along the longitudinal direction and a steering wire arranged at an inside of each flexible tube is linearly arranged may be used in a robot hand design so that the length of the steering wire used for driving each finger is not affected by being pulled or loosened due to the rotation of the wrist.

Hereinafter, a flexible mechanism according to a modified embodiment of the present invention will be described with reference to FIGS. 12 to 14.

Figure 14:
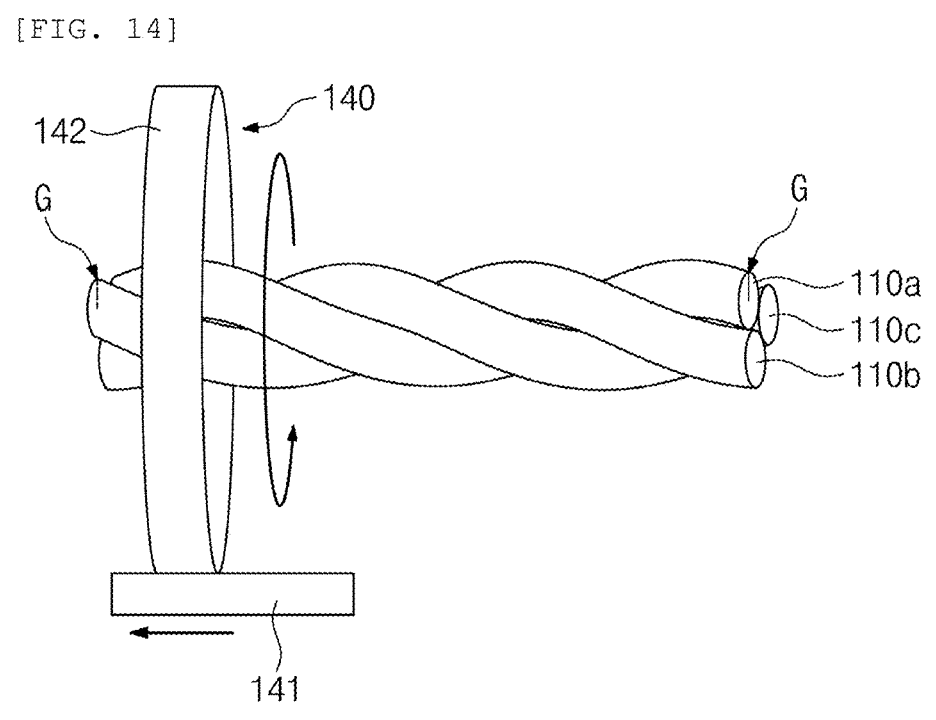

FIGS. 12 to 14 are views for explaining a flexible mechanism according to a modified embodiment of the present invention.

Referring to FIG. 12, a flexible mechanism according to a modified embodiment of the present invention may include means for spirally twisting a first flexible tube 110*a*, a second flexible tube 110*b*, and a third flexible tube 110*c* along the longitudinal direction to make and maintain a flexible tube group 101.

For this purpose, the flexible mechanism according to the modified embodiment of the present invention may include a worm gear 140, a clamping member 150, a worm wheel fixing pin 160, and a mount unit 170.

The worm gear 140 may include the worm 141 and the worm wheel 142 gear-coupled with the worm 141 to rotate in engagement with the worm 141. According to a modified embodiment of the present invention, one longitudinal end of the first flexible tube 110*a*, the second flexible tube 110*b*, and the third flexible tube 110*c* may pass through the center of the inner diameter of the worm wheel 142.

The clamping member 150 may be provided on an inner diameter side of the worm wheel 142. The clamping member 150 may be fastened to an outer circumferential surface at one longitudinal end side of the first flexible tube 110*a*, the second flexible tube 110*b*, and the third flexible tube 110*c* penetrating the center of the inner diameter of the worm wheel 142 to integrally fix the same.

According to a modified embodiment of the present invention, the clamping member 150 may include a first clamp 151, a second clamp 152, and a clamp pressing pin 153.

The first clamp 151 may be fixed to an inner diameter side of the worm wheel 142. The first clamp 151 may support the lower sides (based on the drawing) of the first flexible tube 110*a*, the second flexible tube 110*b*, and the third flexible tube 110*c* while being fixed to an inner diameter side of the worm wheel 142.

The second clamp 152 may support the upper sides (based on the drawing) of the flexible tubes 110*a*, 110*b*, and 110*c* so as to be symmetrical to the first clamp 151 with the first flexible tube 110*a*, the second flexible tube, and the third flexible tube stacked therebetween. In other words, the flexible tubes 110*a*, 110*b*, and 110*c* may be pressed and supported by the first clamp 151 and the second clamp 152 arranged on the upper and lower sides thereof.

The clamp pressing pin 153 may press the second clamp 152. For this purpose, the clamp pressing pin 153 may be connected to the second clamp 152. The clamp pressing pin 153 may be bolt-coupled from a radial outer side to an inner side of the worm wheel 142.

A lower longitudinal end of the clamp pressing pin 153 may be lowered when being bolt-coupled to the worm wheel 142, and then may come into contact with an upper side (based on the drawing) of the second clamp 152. In this case, when the bolt-coupling of the clamp pressing pin 153 is continued, a pressing force of the clamp pressing pin 153 applied to the upper end of the second clamp 152 may be continuously increased at the lower longitudinal end of the clamp pressing pin 153, and accordingly, the flexible tubes 110*a*, 110*b* and 110*c*, of which outer circumferential surfaces are circumferentially surrounded by the first clamp 151 and the second clamp 152 may be pressed and fixed thereby.

As such, the clamp pressing pin 153 may press the second clamp 152 toward the first clamp 151 through a fastening force with respect to the worm wheel 142, and accordingly, the flexible tubes 110*a*, 110*b* and 110*c* may be pressed and fixed between the first clamp 151 and the second clamp 152.

The worm wheel fixing pin 160 may restrict the rotation of the worm wheel 142 by pressing one side of an outer diameter side of the worm wheel 142. When the flexible tubes 110*a*, 110*b* and 110*c* are twisted at a multiple of 360 degrees by the rotation of the worm wheel 142 to form the flexible tube group 101, the worm wheel fixing pin 160 may restrict further rotation of the worm wheel 142 to maintain the twisted structure of the flexible tube group 101.

The worm wheel fixing pin 160 may be mounted on a mount unit 170 and supported by the mount unit 170. In this case, the worm wheel fixing pin 160 may be coupled to the mount unit 170 in a bolt-coupling manner, thereby pressing the outer circumferential surface of the worm wheel 142. In other words, the worm wheel fixing pin 160 may restrict the rotation of the worm wheel 142 through the same mechanism as that of the clamp pressing pin 153.

Referring to FIG. 13, at the time of initial setting, the one longitudinal end of the first flexible tube 110*a*, the second flexible tube 110*b*, and the third flexible tube 110*c*, which are stacked with each other in a linear shape, may pass through the center portion of the worm wheel 142.

One longitudinal end of the flexible tubes 110*a*, 110*b* and 110*c* may be pressed and supported by the clamping member 150 and may be positioned in a form of penetrating the center portion of the worm wheel 142. In this case, the opposite longitudinal ends of the flexible tubes 110*a*, 110*b* and 110*c* may be formed in a fixed state.

Referring to FIG. 14, when the worm gear 140 is operated in this state, the one longitudinal end of the first flexible tube 110*a*, the second flexible tube 110*b*, and the third flexible tube 110*c*, to which the opposite longitudinal ends are fixed, may rotate integrally with the worm wheel 142 of the worm gear 140, and accordingly, the flexible tube group 101 spirally twisted along the longitudinal direction may be formed.

In this case, the worm gear 140 may rotate one longitudinal end of the first flexible tube 110*a*, the second flexible tube 110*b*, and the third flexible tube 110*c* so that a cycle in which the flexible tube group 101 is twisted and wound may become a multiple of 360 degrees, and further rotation may be restricted by the worm wheel fixing pin 160 when completed.

Here, one longitudinal end and the opposite end of the flexible tube group 101, more specifically, one longitudinal end and the opposite end of the first flexible tube 110*a* may be marked with alignment notches G on the same line.

Accordingly, when the flexible tube group 101 is formed by rotating one longitudinal end of the first flexible tube 110*a*, the second flexible tube 110*b*, and the third flexible tube 110*c* through rotation of the worm wheel 142 and spirally twisting the same, it may be easily determined whether or not the cycle in which the flexible tube group 101 is twisted and wound forms a multiple of 360 degrees.

In other words, when the worm wheel 142 is rotated, it may be possible to check whether or not the alignment notches G respectively marked on one longitudinal end and the opposite end of the first flexible tube 110*a* are positioned on the same line, thereby appropriately controlling the degree of rotation of the worm wheel 142.

The fact that the alignment notches G respectively marked on one longitudinal end and the opposite end of the first flexible tube 110*a* are positioned on the same line may mean that the cycle in which the first flexible tube 110*a*, the second flexible tube 110*b*, and the third flexible tube 110*c* are twisted and wound form a multiple of 360 degrees in order to form the flexible tube group 101.

Although the present invention has been described in detail with reference to exemplary embodiments, the scope of the present invention is not limited to a specific embodiment and should be interpreted by the attached claims. In addition, those skilled in the art should understand that many modifications and variations are possible without departing from the scope of the present invention.

The invention claimed is:

1. A multiple helix flexible mechanism comprising:

a plurality of flexible tubes extending in a longitudinal direction, wherein each tube of the plurality of flexible tubes has at least two steering wires linearly arranged in a respective flexible tube in the longitudinal direction so as to transfer an operating force applied to one longitudinal end of the flexible tube to an end effector connected to an opposite longitudinal end of the flexible tube, wherein the plurality of flexible tubes includes at least two flexible tubes, wherein the at least two flexible tubes are twisted in a spiral shape along the longitudinal direction to form a flexible tube group, wherein, when bending occurs in the multiple helix flexible mechanism, the at least two steering wires are movable along the longitudinal direction such that the at least two steering wires are maintained at the same length between the one longitudinal end and the opposite longitudinal end of each of the plurality of flexible tubes, wherein, when at least two end effectors are provided, (i) for each of the end effectors, the at least two steering wires in a corresponding one of the flexible tubes are connected to the respective end effector in one-to-one correspondence, and each of the end effectors is controlled independently without interference with another one of the end effectors, (ii) for each of the end effectors, the steering wires in the corresponding flexible tube that transmit the operating force to the respective end effector are maintained at the same length between the one longitudinal end and the opposite longitudinal end of the corresponding flexible tube, wherein the flexible tube group is coupled to each of the end effectors via a gimbal, wherein the at least two flexible tubes, spirally wound around each other, extend through the gimbal and branch off toward each of the end effectors, and wherein the gimbal provides each of the end effectors with two degrees of freedom of rotation in horizontal and vertical axis directions, and the gimbal is configured to maintain a tension state of the steering wires, arranged inside each of the at least two flexible tubes, without change during rotation of the gimbal.

2. The multiple helix flexible mechanism of claim 1, further comprising:

a flexible shaft extending in a longitudinal direction of the flexible tube group, wherein the at least two flexible tubes are twisted and wound in a spiral shape along a longitudinal direction of an outer circumferential surface of the flexible shaft.

3. The multiple helix flexible mechanism of claim 1, wherein the at least two flexible tubes are alternately twisted and wound in a same cycle.

4. The multiple helix flexible mechanism of claim 3, wherein the cycle in which the at least two flexible tubes are twisted and wound is a multiple of 360 degrees.

5. The multiple helix flexible mechanism of claim 1, wherein each of the plurality of flexible tubes comprises at least one linear tunnel which is provided at an inside of the respective flexible tube in the longitudinal direction, and any one of the steering wires is inserted through any one of the linear tunnels.

6. The multiple helix flexible mechanism of claim 1, further comprising:

a housing tube, wherein the housing tube extends in the longitudinal direction, and the flexible tube group is arranged in the longitudinal direction inside the housing.

7. The multiple helix flexible mechanism of claim 6, wherein a spiral rail for providing a spiral path of the flexible tube group is provided inside the housing tube.

8. The multiple helix flexible mechanism of claim 1, further comprising:

a worm gear including a worm and a worm wheel rotating in engagement with the worm;

a clamping member provided at an inner diameter side of the worm wheel and fastened to an outer circumferential surface at one longitudinal end side of the flexible tube group passing through the inner diameter side of the worm wheel;

a worm wheel fixing pin configured to restrict rotation of the worm wheel by pressing one side of an outer diameter side of the worm wheel so that a twisted structure of the flexible tube group is maintained when the flexible tube group is twisted and wound at a multiple of 360 degrees by the rotation of the worm wheel; and a mount unit for supporting the worm wheel fixing pin.

9. The multiple helix flexible mechanism of claim 8, wherein the clamping member comprises:

a first clamp fixed to the inner diameter side of the worm wheel;

a second clamp arranged to be symmetrical to the first clamp with the flexible tube group interposed therebetween; and a clamp pressing pin connected to the second clamp and configured to press the second clamp toward a first clamp side through a fastening force with respect to the worm wheel to fix the flexible tube group wrapped by the first clamp and the second clamp.

10. The multiple helix flexible mechanism of claim 8, wherein alignment notches are collinearly marked on one longitudinal end and an opposite end of the flexible tube group, in order to determine whether or not the flexible tube group is twisted and wound at the multiple of 360 degrees.

* * * * *